(12) United States Patent
Bielenstein et al.

(10) Patent No.: US 8,647,672 B2
(45) Date of Patent: Feb. 11, 2014

(54) METHOD FOR PRODUCING A CROSS-LINKED POLYACRYLATE POLYMER IMPLANT MATERIAL

(75) Inventors: Oliver Bielenstein, Berlin (DE); Stefan Deusser, Kahl a. Main (DE); Christoph Sattig, Dieburg (DE); Volker Stirnal, Dieburg (DE)

(73) Assignee: AAP Biomaterials GmbH, Dieburg (DE)

( * ) Notice: Subject to any disclaimer, the term of this patent is extended or adjusted under 35 U.S.C. 154(b) by 0 days.

(21) Appl. No.: 13/499,342

(22) PCT Filed: Sep. 20, 2010

(86) PCT No.: PCT/EP2010/005952
§ 371 (c)(1),
(2), (4) Date: Jul. 23, 2012

(87) PCT Pub. No.: WO2011/038906
PCT Pub. Date: Apr. 7, 2011

(65) Prior Publication Data
US 2012/0302648 A1 Nov. 29, 2012

(30) Foreign Application Priority Data

Sep. 30, 2009 (DE) .......................... 10 2009 043 551

(51) Int. Cl.
*A61K 9/14* (2006.01)
(52) U.S. Cl.
USPC ........................................................ 424/487
(58) Field of Classification Search
None
See application file for complete search history.

(56) References Cited

FOREIGN PATENT DOCUMENTS

| EP | 1 366 774 A1 | * 12/2003 |
|---|---|---|
| EP | 1366774 | 12/2003 |
| EP | 1430913 | 6/2004 |

OTHER PUBLICATIONS

International Search Report dated May 10, 2011 corresponding to International Patent Application No. PCT/EP2010/005952.
International Preliminary Report on Patentability dated Apr. 3, 2012 corresponding to International Patent Application No. PCT/EP2010/005952.

* cited by examiner

*Primary Examiner* — Carlos Azpuru
(74) *Attorney, Agent, or Firm* — Ohlandt, Greeley, Ruggiero & Perle, LLP

(57) ABSTRACT

The invention relates to an implant material comprising a polymer which is partially cross-linked by means of a metal acrylate salt.

13 Claims, No Drawings

METHOD FOR PRODUCING A CROSS-LINKED POLYACRYLATE POLYMER IMPLANT MATERIAL

The invention relates to a polymeric implant material and a method for producing it. In particular, the invention relates to a bone cement and an intervertebral disc replacement.

BACKGROUND OF THE INVENTION

Polymeric implant materials are known. Thus, for example, acrylic-based bone cements are used. In particular, methyl methacrylate is used for the formation of a polymethyl methacrylate (PMMA) bone cement.

High strengths can be achieved with bone cements of this type, so that they can also be used in orthopedics. However, acrylic-based bone cements also find use in vertebroplasty and kyphoplasty.

For the most part, thermoplastics are used, thus materials that cannot be cross-linked or can be cross-linked only to a very small extent. In the case of cross-linking cements known in medical technology, there are indications that these have an essentially smaller biocompatibility. Such materials are therefore not usually used.

For the most part, an x-ray contrast agent is added to known bone cements. Zirconium oxide and barium oxide are widely used in practice as x-ray contrast agents. It has turned out that these materials, which are used in particulate form, frequently lead to inclusions of air. In addition, the metal particles that are partly present in a submicron size range may damage the surrounding tissue due to their cytotoxic effect. Finally, due to their abrasive effect, the metal particles can lead to abrasions on the contact surfaces and thus to the formation of free particles. As a rule, this abrasion acts very negatively on the surrounding tissue.

Problem of the Invention

The problem of the invention is to provide an implant material with improved properties.

SUMMARY OF THE INVENTION

The problem of the invention is solved by a method for producing an implant material and by an implant material according to one of the independent claims.

Preferred embodiments and enhancements of the invention can be taken from the respective subclaims.

The invention relates to a method for producing an implant material. The implant material involves a polymeric implant material, in particular a polyacrylate. According to the invention, a polymer, in particular a polyacrylate, is partially cross-linked by means of a partially polymerizable metal salt.

The inventors have discovered that cross-links with improved biocompatibility can be produced via polymerizable metal salts. Based on the cross-links, an implant material with improved mechanical properties can be provided.

In particular, a cross-linking bone cement that has no noteworthy side effects could be provided by the invention. Known approaches for producing cross-linked bone cements from duroplasts or elastomers for the most part have led to undesired side effects of the implant material.

In addition to this, additional functionalities, such as those of an x-ray contrast agent, for example, can be provided by means of the central metal atom.

A metal acrylate is preferably used for cross-linking. It is understood that an acrylate with at least two functional acrylate groups must be used for producing cross-links. Preferably, an acrylate with at least three acrylate groups, and particularly preferred at least four acrylate groups, will be used.

The use of a metal oxalate or a metal (di)maleinate, however, is also conceivable.

In the sense of the invention, a salt with a metalloxy cation, such as $ZrO^{2+}$, for example, is viewed as a metal salt.

In contrast to the known use of zirconium oxide or barium oxide as an additive or aggregate, the metal is bound in the polymer backbone and thus is not present as a particulate oxide, which is accompanied by the disadvantageous effects named above.

Also, the use of metals for other functionalities is also conceivable. Thus, for example, it is conceivable to use a magnesium or calcium salt, in particular, a magnesium or calcium acetate as a cross-linker in order to promote ingrowth. Also, the use of a small amount of a silver salt, for example, the use of silver acetate, is conceivable, in order to thus achieve a bacteriostatic or bactericidal effect.

The following metals find use, in particular: Ca, Sn, Zr, Fe, Mo, Ag, Mn, Co and/or Ti.

The polymerizable metal salt is preferably first dissolved in a monomer, for example in a (meth)acrylate.

In one embodiment of the invention, dissolution in the monomer takes place in such a way that the acrylate is dissolved in a monomer directly in connection with its production. It has turned out that, for example, zirconium acetate powder produced from zirconium acetate and methacrylic acid is well soluble in MMA. In contrast, commercially available zirconium acetate does not dissolve, possibly because this material polymerizes at least partially over time, so that it is no longer soluble in MMA.

In this case, salts of multivalent metals, in particular 4-valent metals, are of advantage, since the four functional acrylate groups screen the central atom so that the metal acrylate has such a small polarity that it dissolves well in a monomer or pre-polymer.

In the production, preferably 5 to 90%, particularly preferred 10 to 50%, of the polymerizable metal salt is used. This percentage refers to the ratio of the polymerizable metal salt relative to the monomers, polymers or pre-polymers otherwise used. Thus, other additives that may be used do not enter into the calculation.

In an enhancement of the invention, first partially cross-linked polymer particles are produced, which are then partially dissolved or swollen in a monomer. Subsequently the implant material is polymerized from the monomer, the polymer particles being cross-linked with the remaining polymer.

This embodiment is particularly suitable for providing bone cement. In this case, as described above, a partially cross-linked polymer, for example in the form of a pearl polymer, is produced first. It is understood that this polymer may also be only partially polymerized.

The particles are cross-linked with a monomer in a second step, which may occur in vivo, for example, the particles being bound in the forming polymer backbone, due to the partial dissolution or swelling.

First of all, this embodiment of the invention has the advantage that, due to the added polymer particles, a paste can be provided, which is dimensionally stable due to its consistency and thus can be well processed as cement. In addition, a high proportion of the implant material is already polymerized before it is introduced. Because of the additional polymerization by means of the monomer, the hardening of the implant material thus occurs more rapidly and at lower temperature.

In an enhancement of the invention, the partially cross-linked polymer is added to a solvent, whereby components that are not cross-linked at least partially dissolve out and thus a porous structure is formed. Because of the long-chain components that are dissolved out, a microporous foam structure is created having channel-like, at least partially open-pore structures.

The thus-produced article can possess a high elasticity and is thus also suitable, for example, for use as an intervertebral disc implant. In addition, the porous structure can be used for introducing an active substance, for example an antibiotic.

Conventional implant materials containing an active substance often have the disadvantage that in the initial period after insertion, the active substance is released in a high dose, but afterward only slowly diffuses out from the implant material. This disadvantage can be at least reduced by the above-named embodiment of the invention.

Preferably, between 20 and 80% of the volume of the implant material is dissolved out.

In a preferred embodiment of the invention, an initiator, in particular dibenzoyl peroxide, and an accelerator, in particular dimethyl-p-toluidine, are added for the polymerization.

By addition of initiator and accelerator, in particular for use of the implant material as a bone cement, in which the polymerization occurs at least partially in vivo, the polymerization can be accelerated in such a way that even after a short time, a sufficient strength is achieved. In addition, starting from when a polymerization occurs, the temperature can be reduced to a temperature that does not damage tissue.

The invention, in addition, relates to an implant material that can be produced with a method described above.

The invention relates to an implant material, in particular bone cement, comprising a polymer that is cross-linked via a central metal atom. It has turned out that cross-links that are provided via a central metal atom do not lead to undesired side effects.

Further, the invention relates to an implant that comprises a polyacrylate that is partially cross-linked via a metal acrylate group.

An implant material with improved properties can be provided via metal acrylate groups, which bring about a partial cross-linking. In particular, the mechanical properties can be improved.

In an enhancement of the invention, components that are not cross-linked are at least partially dissolved out. The implant has a porous, in particular microporous, structure.

In a preferred embodiment of the invention, an at least 4-valent metal atom forms the central atom of the cross-links.

The average molecular weight is preferably between $1 \times 10^5$ and $1.5 \times 10^6$ g/mol. The average molecular weight is preferably essentially normally distributed.

The invention is particularly suitable for providing a bone cement.

In particular, a bone cement is provided, in which barium, zirconium or titanium is bound as the central atom of the cross-links and which thus has an x-ray contrast agent bound molecularly in the polymer backbone.

Further, the invention can be used for an intervertebral disc replacement, in which the implant material is porous and elastic.

The invention will be explained in more detail below on the basis of two embodiment examples.

EXAMPLE 1

First, a zirconium acrylate is dissolved in (methyl) methacrylic acid, and a partially cross-linked polymer is produced, for example, by increasing the temperature. The polymer can then be milled into a pearl polymer or a pearl polymer can be produced directly in a suspension polymerization. The fraction of cross-links can be controlled via the quantity of (methyl) methacrylic acid or methyl (acrylic acid). Thus, an excess of methacrylic acid, for example, leads to a smaller fraction of cross-links.

It is understood that additional substances, such as initiators or accelerators, for example, can be used in the polymerization.

For mixing a bone cement, the pearl polymer is mixed into a paste with methyl methacrylate with addition of dimethyl-p-toluidine as an accelerator and dibenzoyl peroxide as an initiator.

The paste is then processed as a bone cement and introduced into defect sites, for example, by means of a syringe or by hand.

Components of the pearl polymer that are not cross-linked by the methyl methacrylate are partially dissolved and the pearl polymer is bound in the polymer backbone.

Due to the zirconium bound in the polymer backbone, the bone cement comprises an x-ray contrast agent, so that particulate metal oxide additions can be dispensed with.

EXAMPLE 2

First, similar to what is described above, a metal acrylate is dissolved in methyl methacrylate and then a partially cross-linked polymer is produced.

For example, components that are not cross-linked are then at least partially dissolved out by means of methacrylic acid as a solvent.

A porous molded object is formed, which can be used, for example, for the (partial) replacement of an intervertebral disc.

The invention claimed is:

1. A method of producing an implant material, comprising the step of cross-linking a polymer with a polymerizable metal salt by dissolving said polymerizable metal salt in an acrylic monomer to produce a cross-linked polyacrylate polymer via polymerization.

2. The method of claim 1, wherein said polymerizable metal salt is a metal acrylate.

3. The method of claim 2, wherein said metal acrylate includes a metal selected from the group consisting of Ba, Sr, Mg, Zn, Sn, Cu, Zr, Fe, Cr, Mo, Mn, Co, Ti, and any combinations thereof.

4. The method of claim 1, wherein said polymerizable metal salt is an acrylate having at least one four-valent central atom.

5. The method of claim 1, wherein during said producing step, 10 to 50% of the polymerizable metal salt is used.

6. The method of claim 1, further comprising the steps of:
producing partially cross-linked polymer particles of said partially cross-linked polymer;
partially dissolving or swelling said polymer particles in a monomer; and
polymerizing the implant material from said monomer, wherein said polymer particles are cross-linked with the partially cross-linked polymer.

7. The method of claim 1, further comprising the step of adding said partially cross-linked polymer to a solvent, wherein portions of said partially cross-linked polymer that are not cross-linked are at least partially dissolved out and a porous structure is formed.

8. The method of claim 7, further characterized in that between 20 and 80% of the volume of the implant material is dissolved out.

9. The method of claim 7, wherein said porous structure is used as a support for an active substance.

10. The method of claim 1, further comprising the step of adding an initiator and an accelerator during said producing step.

11. The method of claim 10, wherein said initiator is dibenzoyl peroxide, and said accelerator is dimethyl p-toluidine.

12. The method of claim 1, wherein said acrylic monomer is a methacrylate.

13. The method of claim 1, wherein said acrylic monomer is a methacrylic acid.

* * * * *